United States Patent
Richard et al.

(10) Patent No.: US 8,257,360 B2
(45) Date of Patent: Sep. 4, 2012

(54) DETERMINING FEMORAL CUTS IN KNEE SURGERY

(75) Inventors: Alain Richard, Montreal (CA); Patrick Garceau, Lachine (CA); Simon-Paul Dominati, Marseilles (FR)

(73) Assignee: Orthosoft Inc., Montreal, Quebec (CA)

( * ) Notice: Subject to any disclaimer, the term of this patent is extended or adjusted under 35 U.S.C. 154(b) by 1525 days.

(21) Appl. No.: 10/511,261

(22) PCT Filed: Apr. 30, 2003

(86) PCT No.: PCT/CA03/00604
§ 371 (c)(1),
(2), (4) Date: Aug. 15, 2005

(87) PCT Pub. No.: WO03/092522

PCT Pub. Date: Nov. 13, 2003

(65) Prior Publication Data

US 2006/0015120 A1    Jan. 19, 2006

(30) Foreign Application Priority Data

Apr. 30, 2002 (WO) ................ PCT/CA02/00638

(51) Int. Cl.
*A61B 17/58* (2006.01)
*A61B 17/60* (2006.01)
*A61F 2/00* (2006.01)

(52) U.S. Cl. ............... 606/88; 606/87; 606/102

(58) Field of Classification Search ............... 606/102, 606/53

See application file for complete search history.

(56) References Cited

U.S. PATENT DOCUMENTS

| 4,718,413 A * | 1/1988 | Johnson .................. 606/82 |
| 5,649,929 A * | 7/1997 | Callaway .................. 606/88 |
| 5,871,018 A | 2/1999 | Delp et al. |
| 2003/0069591 A1 * | 4/2003 | Carson et al. .............. 606/130 |
| 2005/0049524 A1 | 3/2005 | Lefevre et al. |

FOREIGN PATENT DOCUMENTS

| DE | 100 31 887 | 1/2002 |
| EP | 0 919 203 | 6/1999 |
| EP | 1 226 788 | 7/2002 |
| WO | WO 99 60939 | 12/1999 |
| WO | WO0054687 | 9/2000 |

OTHER PUBLICATIONS

Fixed-Versus Mobile-Bearing Total Knee Arthroplasty: Technical Issues and Surgical Tips (Lawrence S. Crossett, MD, Orthopedics: Feb. 2002; 25).*
Orthopedics, Fixed—Versus Mobile—Bearing Total Knee—Lawrence S. Crossett, MD, Apr. 16, 2003, pp. 1-10.

* cited by examiner

*Primary Examiner* — Thomas Barrett
*Assistant Examiner* — Christine Nelson
(74) *Attorney, Agent, or Firm* — Norton Rose Canada LLP (57) ABSTRACT

There is provided a method and system for determining a distal cut thickness and posterior cut thickness for a femur in a knee replacement operation, the method comprising: performing a tibial cut on a tibia; performing soft tissue balancing based on a desired limb alignment; measuring an extension gap between the femur and said tibial cut while in extension; measuring a flexion gap between the femur and the tibial cut while in flexion; calculating a distal cut thickness and a posterior cut thickness for the femur using the extension gap and the flexion gap and taking into account a distal thickness and posterior thickness of a femoral implant; and performing said femoral cut according to the distal cut thickness and posterior cut thickness.

13 Claims, 11 Drawing Sheets

DETERMINING FEMORAL CUTS IN KNEE SURGERY

FIELD OF THE INVENTION

The invention relates to the field of computer-assisted surgery or image-guided surgery. More specifically, it relates to determining cuts to be made distally and posteriorly to the femur when performing knee surgery.

BACKGROUND OF THE INVENTION

As technology allows us to advance in the field of computer-aided surgery, such systems are becoming more specialized and refined. The advances made for orthopedic surgery are particularly impressive. These systems allow surgeons to prepare for surgery by viewing 3D models of patients' anatomy that were reconstructed using pre-operative images such as scans and x-rays. Virtual planning markers can be inserted into three-dimensional images at any sites of interest and the ideal implant or prosthesis can be designed for a specific patient by constructing virtual implant models and simulating the results with the reconstructed model.

Furthermore, during surgery, many surgical instruments are now tracked and can be displayed on an image of the bone to provide surgeons with a reference as to where they are within a patient's body. This is a precious asset in surgeries that involve delicate procedures that allow the surgeon very little room to maneuver.

A particular procedure for which computer assisted surgery has made quite some headway is in knee surgery. There now exists systems which can indicate how to position the cutting guides in order to produce the desired cuts, and what the bones will look like after the prosthesis has been inserted.

However, it has been found that even with all of the advances in the field of computer assisted surgery for knee surgery, there are still issues with respect to the comfort of the implant for the patient and the duration of the implant in suitable condition to perform its designated function. The life-span of an implant or a prosthesis is dependent on the wear and tear to which it is submitted. In order to reduce the damage done to an implant over the years, the cuts on the bones on which the implants will be placed must be made to an infinitely small precision. Traditionally, this task is performed manually by the surgeon and is dependent on the surgeon's expertise.

Therefore, it would be advantageous to design a system which would automatically determine where the cuts on a bone were to be made and to a precision not afforded by even the most skilled surgeon.

SUMMARY OF THE INVENTION

An object of the present invention is to optimize the placement of an implant or prosthesis in knee replacement operations in order to extend the lifetime of the implant to its maximum.

According to a first broad aspect of the present invention, there is provided a method for determining a distal cut thickness and posterior cut thickness for a femur in a knee replacement operation, the method comprising: performing a tibial cut on a tibia; performing soft tissue balancing based on a desired limb alignment; measuring an extension gap between the femur and the tibial cut while in extension; measuring a flexion gap between the femur and the tibial cut while in flexion; calculating a distal cut thickness and a posterior cut thickness for the femur using the extension gap and the flexion gap and taking into account a distal thickness and posterior thickness of a femoral implant; and performing a femoral cut according to the distal cut thickness and the posterior cut thickness.

Preferably, the distal cut thickness and the posterior cut thickness are calculated such that a post-cut gap from the tibia to the femur is equal in extension and in flexion, i.e. the gaps are balanced. Also preferably, performing a tibial cut comprises obtaining a tibial cut that is substantially perpendicular to a mechanical axis of said limb and the femoral cut is then performed such that it is parallel to the tibial cut. This way, the gaps are rectangular.

According to a second broad aspect of the present invention, there is provided a system for determining a distal cut thickness and posterior cut thickness for a femur in a knee replacement operation, the system comprising: a computer memory for holding data relating to size and shape of at least one tibial implant and at least one femoral implant; a measurement module, for measuring an extension gap between the femur and the tibia while in extension and a flexion gap between the femur and the tibia while in flexion and generating measurement data; a computing module receiving the measurement data and calculating a distal cut thickness and a posterior cut thickness for the femur using the extension gap and the flexion gap and taking into account a distal thickness and posterior thickness of a femoral implant; and an output device for outputting the measurement data and calculated data calculated by the computing module.

Preferably, the computing module calculates the distal cut thickness and the posterior cut thickness such that a post-cut gap from the tibia to the femur is equal in extension and in flexion.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

The life-span of an implant or a prosthesis is dependent on the wear and tear to which it is submitted. In order to reduce the damage done to an implant over the years, it is desirable to perform soft tissue and gap balancing in the knee when placing the implant. Soft tissue balancing refers to the release of the ligaments which hold the femur and tibia together such that the tension in the medial and lateral ligaments is substantially even. This provides an ideal limb alignment for the femur and tibia. Symmetric gap balancing refers to the gap between the femur and the bone left after the tibia and the femur have been cut and before the implants have been placed. It is desirable to have the gap rectangular, i.e. symmetric, as well as equivalent in flexion and in extension, i.e. balanced.

In accordance with the invention described herein, a system is provided to automatically calculate the distal cut thickness and posterior cut thickness to be done to the femur. The system also helps in obtaining soft tissue balancing.

Figure 1:
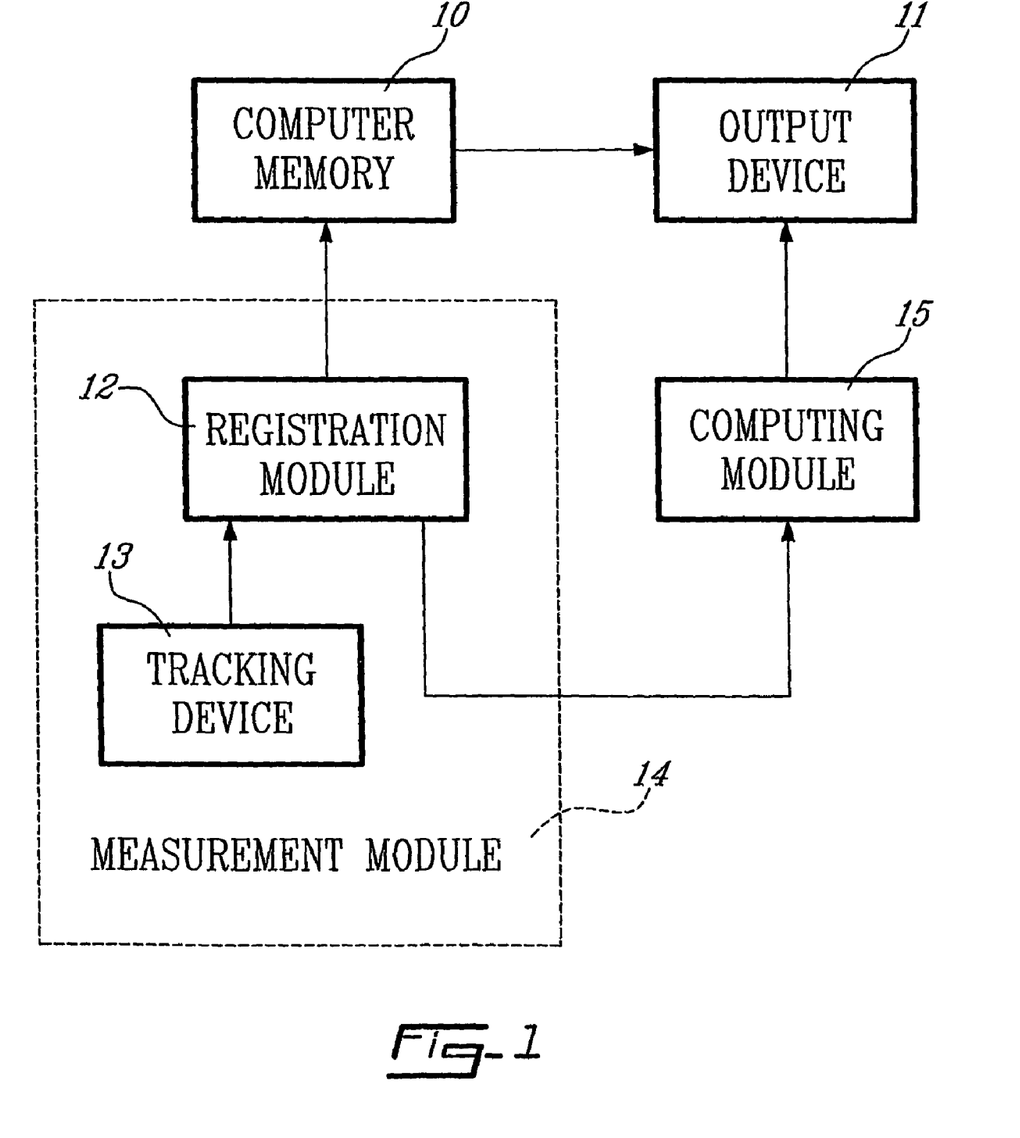
FIG. 1 is a block diagram of a preferred embodiment of the system.

FIG. 1 is a schematic block diagram of the system according to the invention. A computer memory 10 is provided to store data relating to size and shape of different models of tibial and femoral implants that can be used for the operation. The computer memory 10 is also for holding a reference coordinate system and any data registered to the reference coordinate system. If the system is used with a computer-tomography based technique, this means that ct-scans of the femur and tibia are taken pre-operatively and three-dimensional reconstructions are made of the femur and tibia. The computer memory 10 stores these reconstructions for the operation. These reconstructions are then displayed on the output device 11 provided with the system. This output device 11 can be a conventional screen or monitor, a touch screen display, or any equivalent type of output device known to a person skilled in the art.

A registration module 12 is used to register the actual femur and tibia to the virtual bones displayed in the reference coordinate system. This is done using a pointer or digitizer to register important features of the femur and tibia to their respective virtual representations in order to match them. After the tibial cut is made, it is registered into the computer memory 10 as well.

A tracking device 13 is used in conjunction with the registration module. Many variants of tracking devices may be used, such as laser systems, magnetic systems, ultra systems, and active systems, but in the preferred embodiment, an infrared camera is used with markers placed on the bones. The markers are preferably sets of at least three infrared reflective devices placed in a known configuration so that the camera can track them and thereby track the bones in position and orientation. Data from the tracking device 13 is sent to the registration module 12 which in turn sends data to the computer memory 10 for storing. The computer memory 10 then sends the data to the output device 11 for displaying. Alternatively, the system is used with a ct-less technique. In this case, no images of the bones are taken pre-operatively and the virtual representations of the tibia and the femur is done during the operation.

The registration module 12 and tracking device 13 are part of a measurement module 14, present in the system to take measurements on the gaps between the tibia and the femur while in flexion and in extension. A computing module 15 uses the measurements to compute a distal cut thickness and a posterior cut thickness.

The computing module 15 receives measurement data from the measurement module 14 and calculates a distal cut thickness and a posterior cut thickness for the femur using measurements relating to extension gap and flexion gap of the bones and taking into account a distal thickness and posterior thickness of a femoral implant. In one embodiment, the computing module fixes the posterior cut thickness, the distal thickness, and the posterior thickness and calculates the distal cut thickness. The posterior cut thickness may be fixed in response to a user-inputted minimum posterior cut thickness. That is, if the bone is severely damaged and at least a minimum amount must be cut, then this information may be inputted into the computing module and taken into account for the calculations. The user may also select various implant sizes, kept in a database in the computer memory 10 and the selected sizes are considered by the computing module for the calculation. It may be the computing module which accesses the computer memory to select the implant size that best fits the cuts that are to be made on the bones, or the user selects the implant size and fixes it in the computing module. In another embodiment, the computing module performs the calculations for the cut thicknesses in order to obtain balanced gaps. This requirement can be set by the user or pre-programmed into the system.

Figure 2:
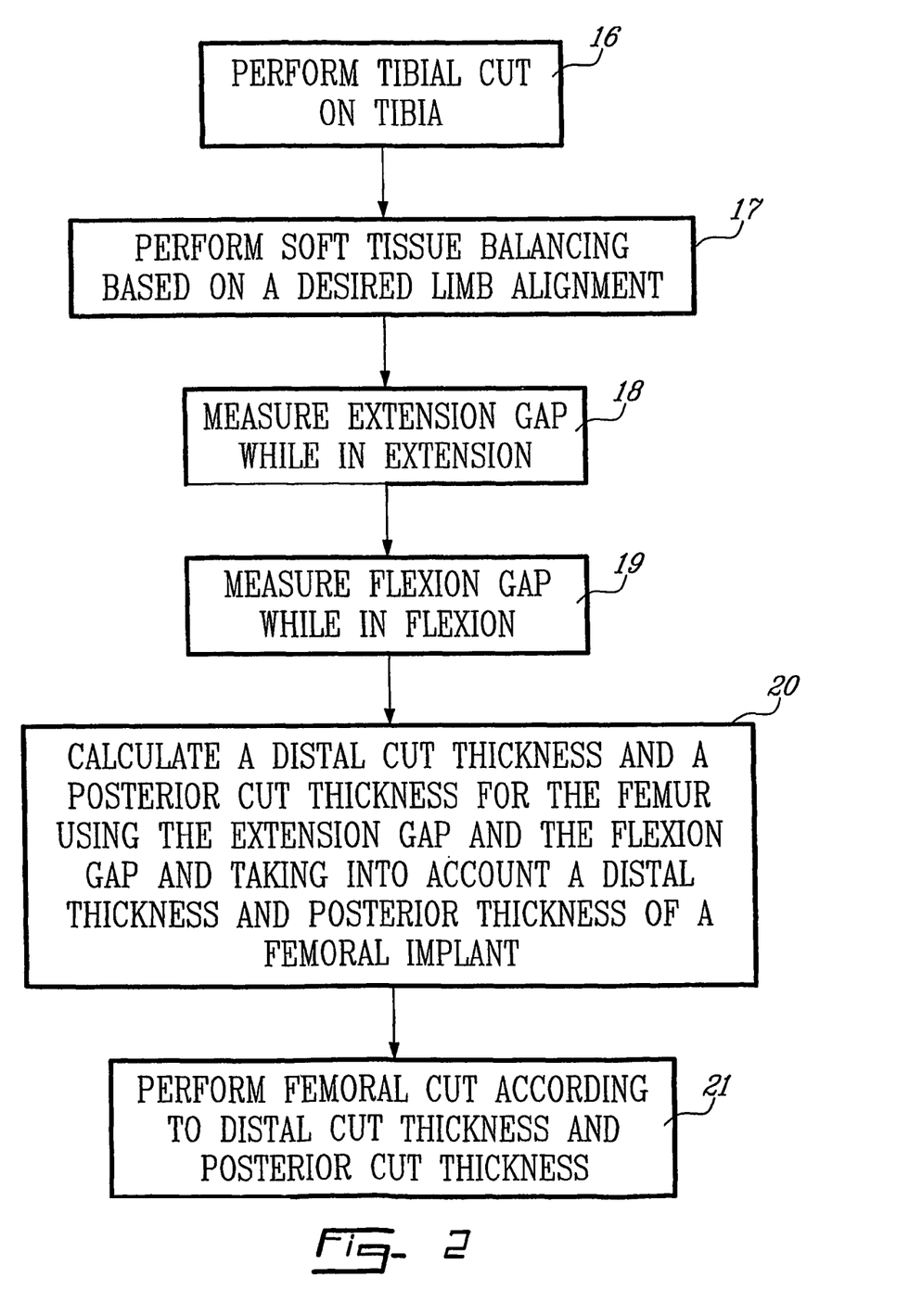
FIG. 2 is a flowchart of the method according to the invention.

FIG. 2 is a flowchart describing the steps used to determine a distal cut thickness and a posterior cut thickness for the femoral cuts to be made on a femur in a knee operation. The first step is to perform the tibial cut 16. This is done first because the calculations that follow are independent of the thickness of the cut made. Therefore, the tibial cut is done in accordance with the expertise of the surgeon to remove all of the bone that is necessary. Soft tissue balancing is then done on the knee based on a desired limb alignment 17. The desired limb alignment may either be calculated by the computer assisted surgery system used, or it may be in accordance with the expertise of the surgeon. The limb is extended and a measurement is taken of the extension gap 18. This gap is from the tibial plateau formed by the tibial cut to the lower tip of the femur. The limb is then flexed and a measurement is taken of the flexion gap 19. This gap is again from the tibial plateau formed by the tibial cut and to the lower tip of the femur. The tissue surrounding the knee affects the gap between the two bones differently while in extension versus flexion. This is why the measurement must be taken in the two positions separately. The next step is to perform the calculations for the distal cut thickness and the posterior cut thickness of the femur using the extension gap and the flexion gap and taking into account a distal thickness and posterior thickness of a femoral implant 20. The calculated cut thicknesses are then used in performing the femoral cuts 21.

Figure 3:
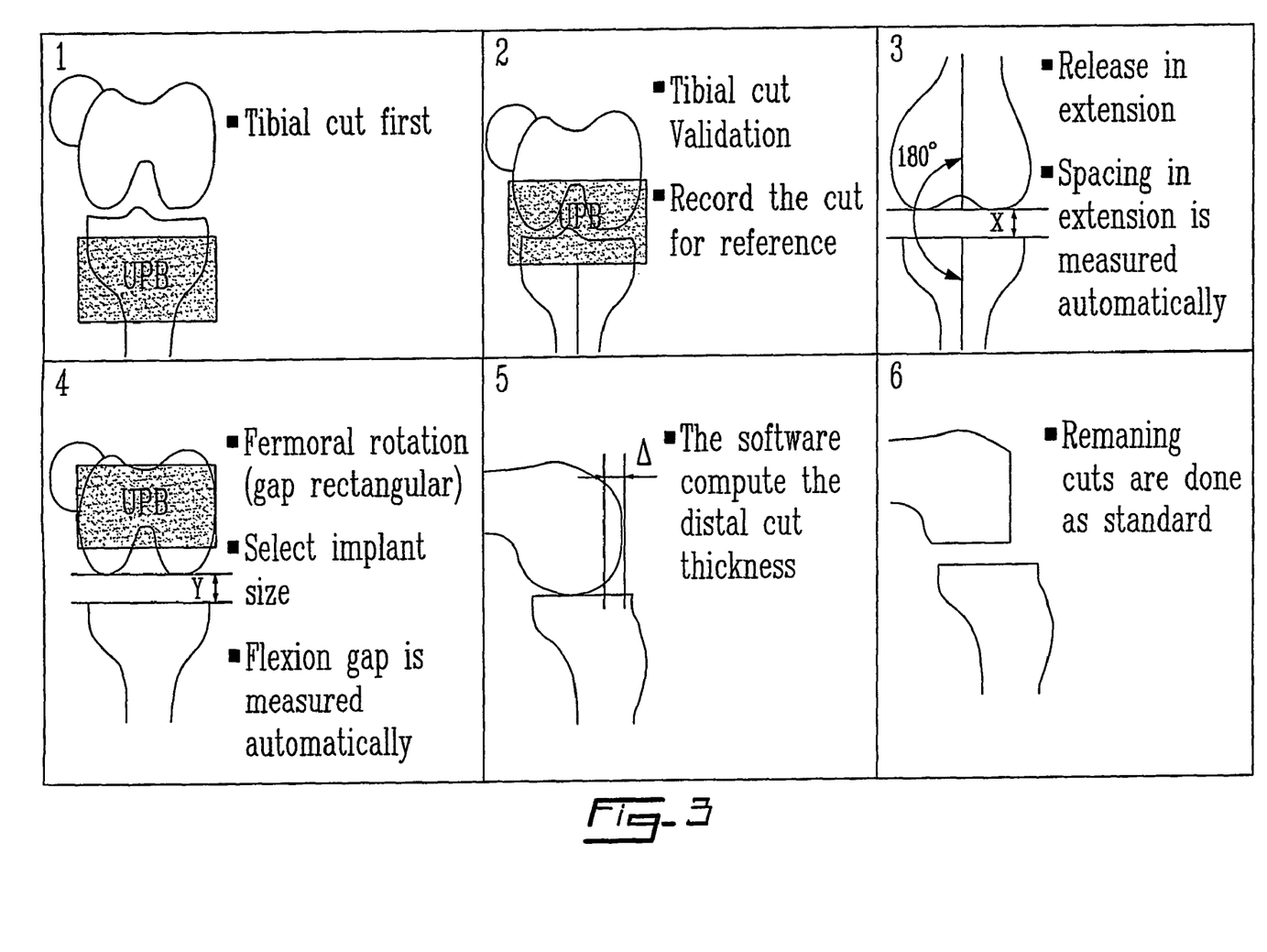
FIG. 3 is a diagram describing the soft tissue and gap balancing technique.
Figure 11:
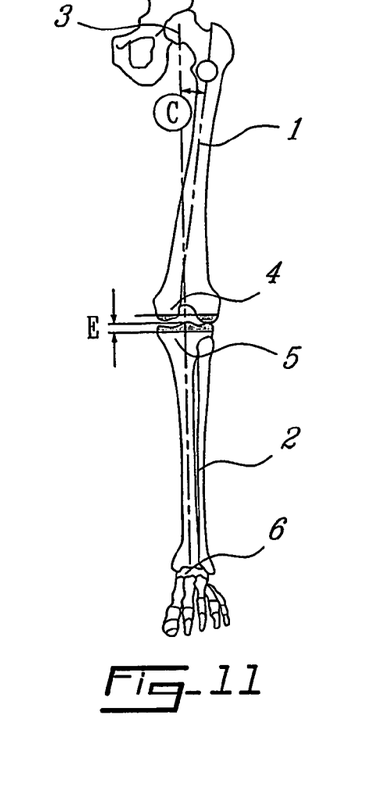
FIG. 11 is an illustration of an anatomically aligned leg.

FIG. 3 demonstrates a technique used to calculate the distal cut thickness required in order to achieve soft tissue and gap balancing in the knee. A tibial cut is first made using standard techniques. A positioning device, or universal positioning block, is used to align the cut to be made with the mechanical axis through the tibia, as seen in FIG. 11. Ideally, the cut is made substantially perpendicular to the mechanical axis. The minimum resection level is chosen by the surgeon such that the damaged portion of the bone is removed without removing more than is judged necessary.

Once the cut has been done, it is then validated and recorded for reference. This means that the cut is registered with the registration module of the computer assisted surgery system. In a preferred embodiment, the system creates a plane along the surface of the tibial cut to represent the cut.

The surgeon must then apply some pressure, either manually or using a tensing device, to the knee in order to allow the femur and tibia to return to their natural positions. When done manually, the surgeon uses his fingers to space the femur and tibia apart and provide tension to the medial and lateral tissues of the knee. Alternatively, a spacer or a tensor can be placed in the area between the femur and tibia to mechanically separate the two and tense the tissues.

The surgeon extends the leg to place it in a fully extended position with the tensor device in position. In this position, the actual mechanical axis of the leg is determined by the system.

The display shows the difference between the actual mechanical axis and a desired mechanical axis for the leg. The surgeon can then see what needs to be done to the medial and lateral tissues to obtain the anatomically correct mechanical axis. This is usually done by the surgeon with a scalpel by releasing either the medial or lateral ligament so as to realign the tibia and femur in a more desirable position. Since the bones are tracked in space, the system can then indicate what the new mechanical axis is after the adjustment to the soft tissues has been done. This method balances the soft tissues in the knee.

Once the adjustment to the soft tissues is complete, a measurement is taken of the distance between the tibia and the femur. In a preferred embodiment, a virtual plane is translated upwards from the tibial cut until it reaches a most posterior point of the reference of the femur. The distance between the tibial cut and the most posterior point of the femur is then measured. Alternatively, a pointer can be used to register a point to use on the tibial plane formed by the cut and a point to use on the femur so as to measure the distance between the two points.

The surgeon is then asked by the system to flex the leg into a substantially 90° position. The system will indicate to the surgeon by way of either an audio sound or an indication on the display that the leg is within a predetermined margin of a 90° position. Another measurement is taken of the distance between the femur and the tibia while in a flexed position.

If a rectangular gap is desired by the surgeon, a universal positioning block is used to provide an upper plane that is parallel to the tibial cut. This plane will determine a posterior cut of the femur.

In a preferred embodiment, all of the implants for the femur have a standard posterior thickness and the distal thickness is equal to the posterior thickness. This standard posterior thickness is used by the computing module 15 as a femoral implant size thickness and is taken into account in the calculation of the distal cut thickness. The computing module 15 calculates the distal cut thickness by adding the measurement taken while in flexion to the femoral implant size constant and subtracts the measurement taken while in extension. The distal thickness of the implant may also be considered in the calculation. The remaining cuts are done using standard techniques known to persons skilled in the art.

Figure 4:
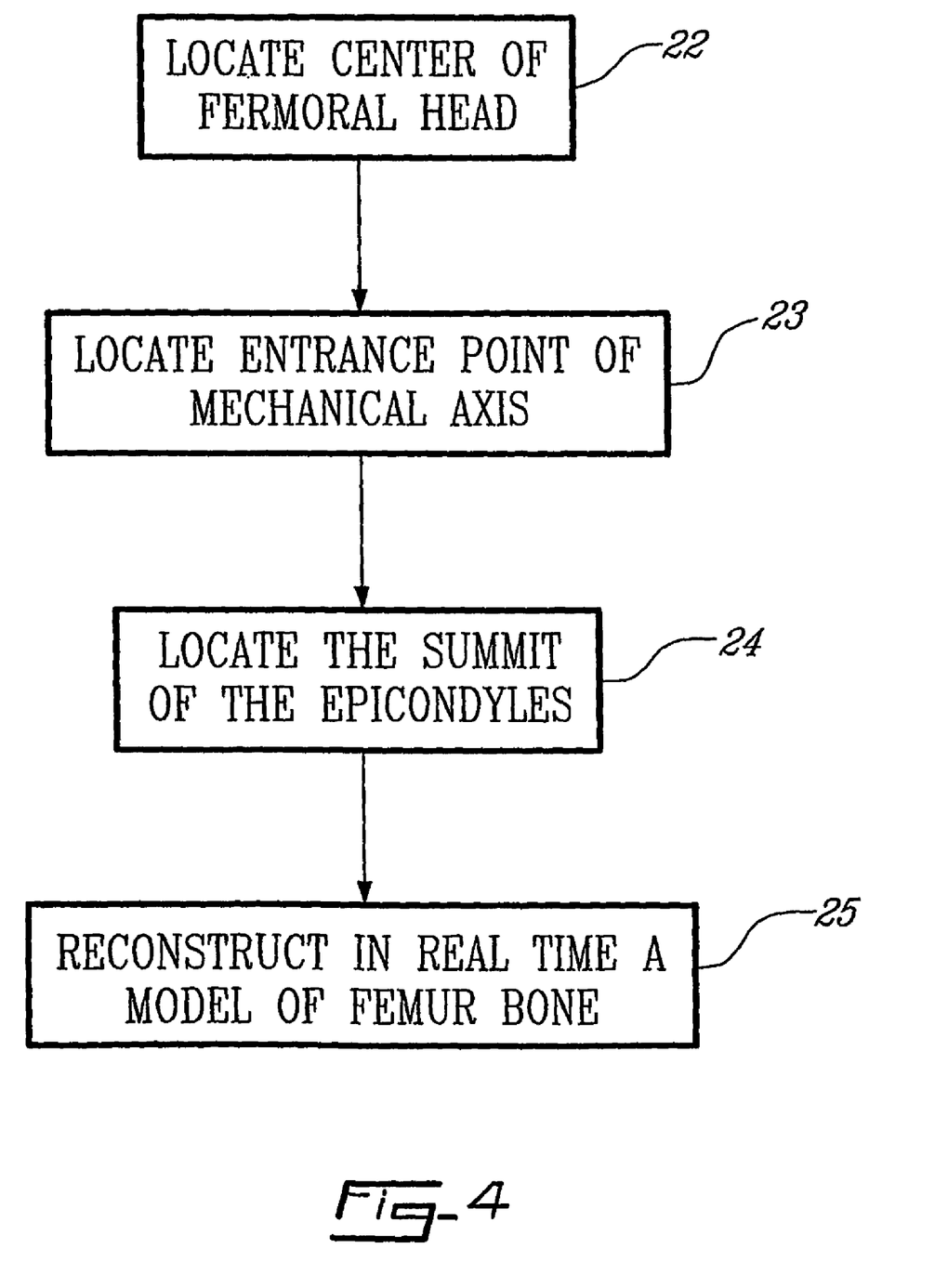
FIG. 4 is a flowchart of the real time reconstruction of a bone model.

FIG. 4 is a flowchart describing the steps used to reconstruct the femur bone during surgery. The first step is to locate the center of the femoral head 22. This point will be used in calculating the mechanical axis. Also needed to calculate the mechanical axis is locating the entrance point of the mechanical axis 23. This point is in the notch found at the exposed end of the femur bone. The surgeon attempts to locate this point by physically palpating the area and once the center is located, this point is digitized by the registration tool and recorded in memory of the system. The next step involves locating the summits of the epicondyles 24. This is also done by the surgeon palpating the two epicondyles on the bone and locating the summits. These two points are then digitized using the registration tool and kept in memory. These three steps allow for the real-time reconstruction of a model of the femur bone 25. Each of these steps will be described in more detail below.

Figure 5:
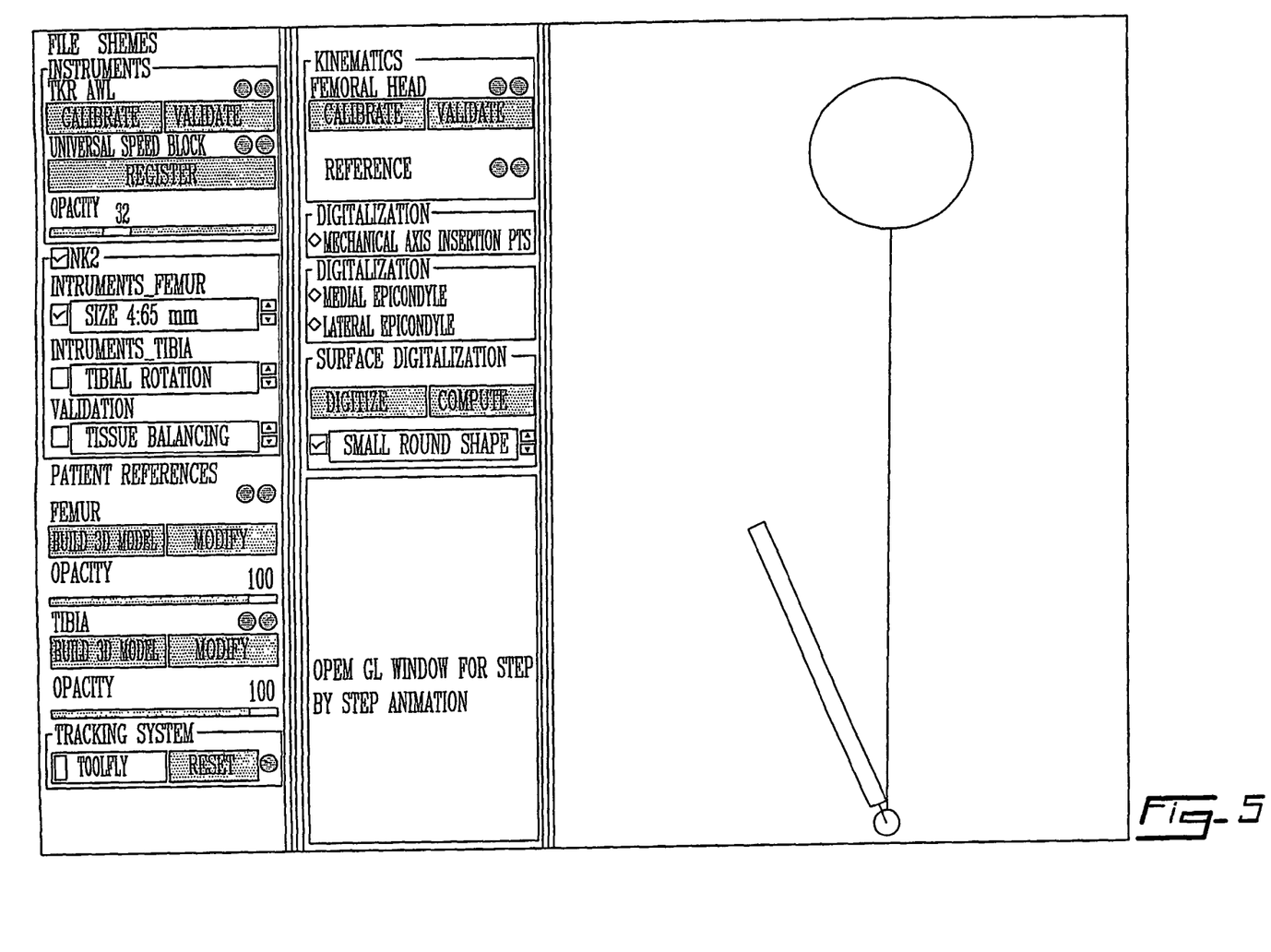
FIG. 5 shows the center of the femoral head and the mechanical axis.

The large sphere in FIG. 5 represents the center of the femoral head. Kinematics are used to locate the center of the femoral head by rotating the femur bone in a circular motion. The pattern of the rotation is registered and the center of rotation is identified as the center of the femoral head. In order for the movement of the bone to be registered, a position sensor must be placed on the bone and a reference is be placed elsewhere on the body, such as on the pelvis bone in case the hip moves. Each movement of the bone with respect to its reference can them be identified in a position tracking system. The center of the sphere, which appears on the screen of an output device, is kept in memory. A registration tool is then used to digitize the entrance point (see FIG. 8) of the mechanical axis in the femur bone. A grid (not shown) can help the surgeon locate the entry point of the mechanical axis. A stretchable line that originates at the center of the sphere and moves with the registration tool represents the mechanical axis. This feature allows the user to correct the location of the femoral mechanical axis by clicking on the mechanical entrance point and changing its position. This axis is used as the main axis of the reference system.

Figure 6:
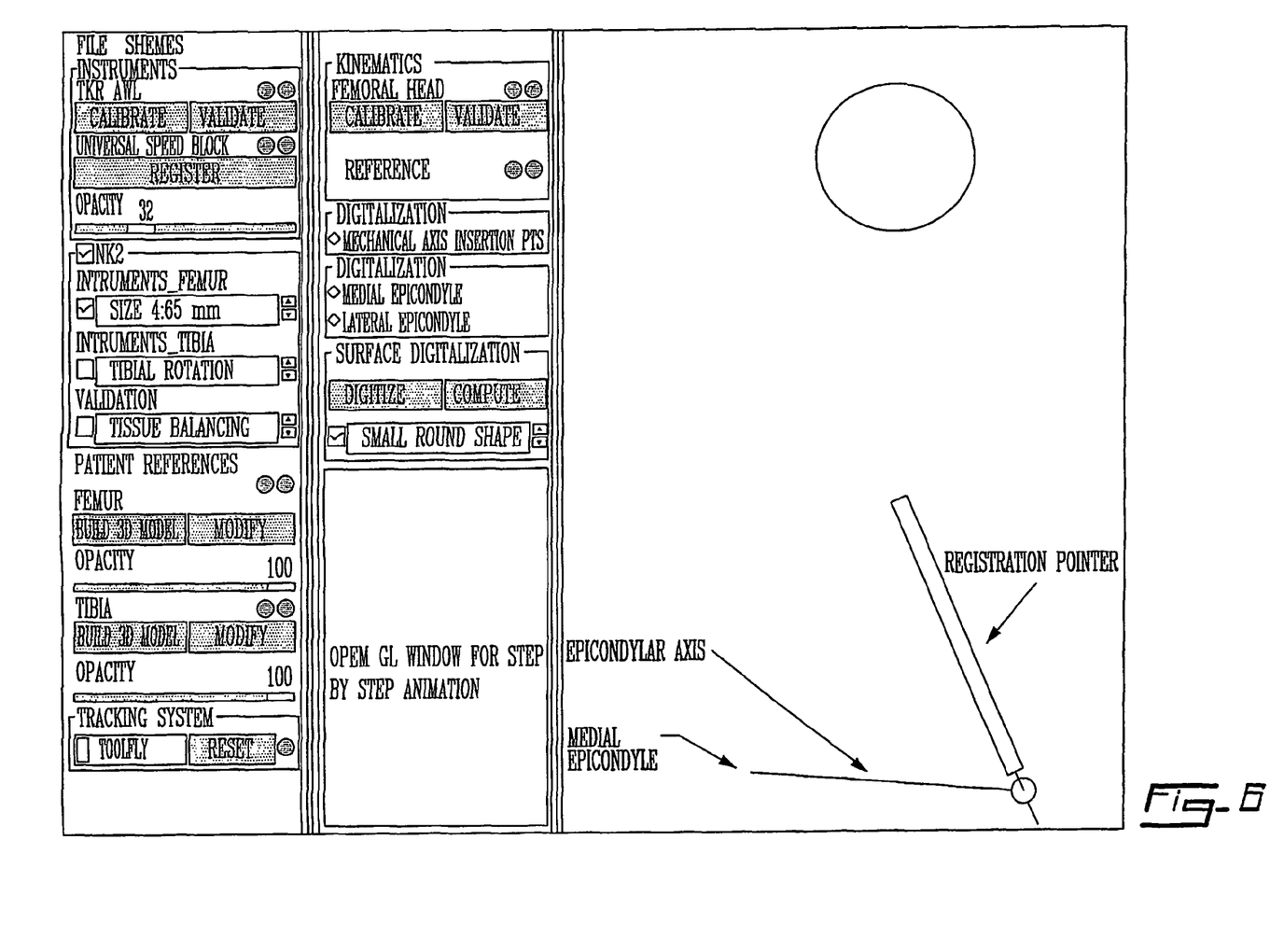
FIG. 6 shows the epicondyles and the epicondylar axis.

The next operation is the digitizing of the epicondyles, as can be seen in FIG. 6. Two points are used to describe a 3D axis by digitizing the epicondyles using the registration tool. The line formed between the epicondyles represents the epicondylar axis. The user can easily modify the two endpoints at any moment. The epicondylar axis is used as the second axis of the reference system.

Figure 7:
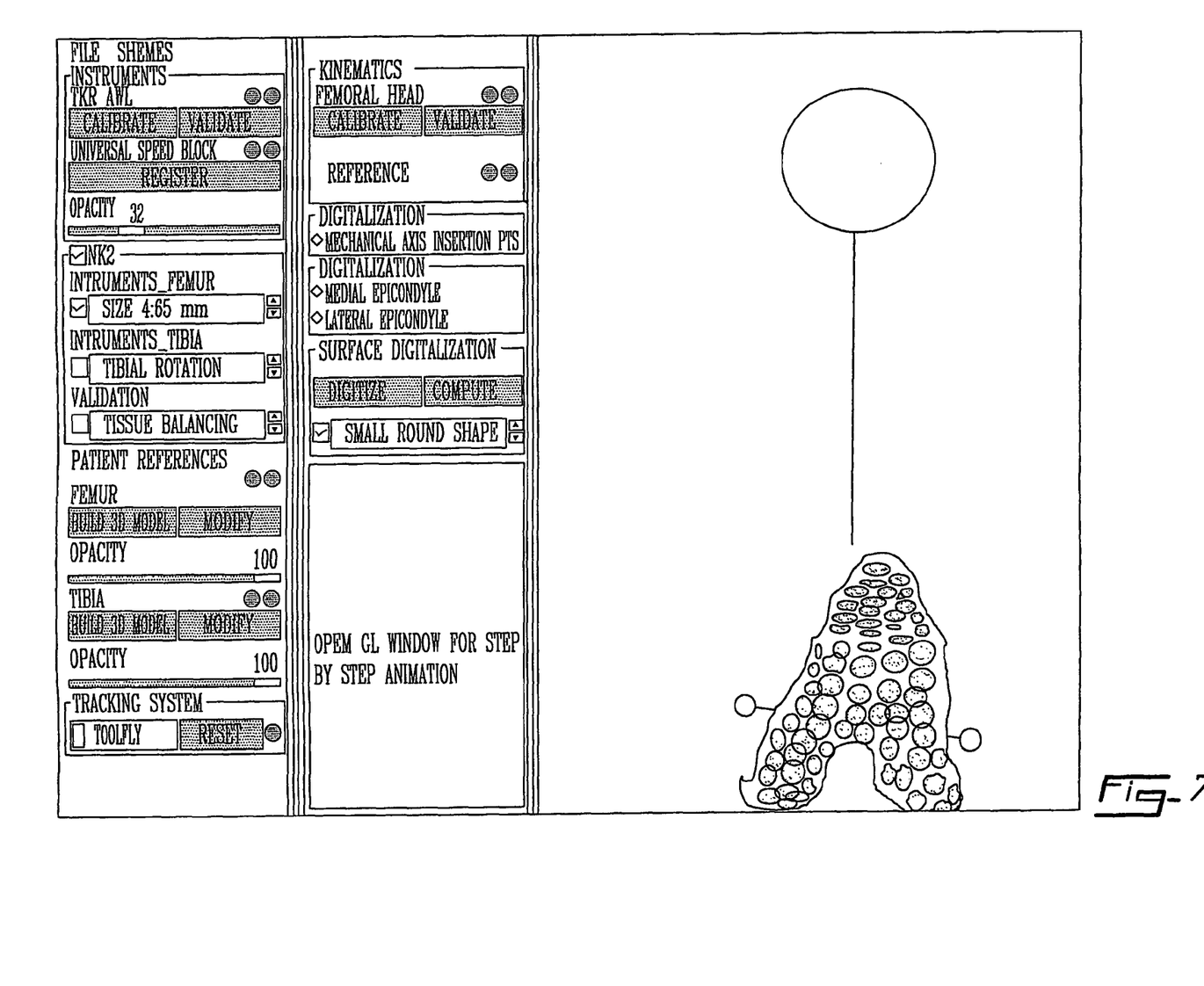
FIG. 7 shows the mosaic reconstruction of a bone.

The surface model reconstruction is a process that allows the user to digitize small surfaces instead of points only. These surfaces can be small circles, as can be seen from FIG. 7. The small circle is physically present on the tip of the registration tool as a small, flat disc. The size of the disc (radius) is chosen as a compromise between accuracy and time. It is counter-productive to ask a surgeon to take hundreds of points when digitizing the surface of a bone. However, the more points taken, the better the representation of the bone and the more accurate the model. The size can also vary depending on the morphology of the bone surface, affecting the precision of the tool. For example, the disc could cover an area of 1 $cm^2$. The disc must be flat on the surface to register as much surface as possible. The tool also registers the normal at the point of contact between the flat disc surface and the bone. When each digitized surface has been registered, an approximate model is displayed on an output device. The model is formed as a mosaic of circular surfaces. This reconstruction is done in real time.

Figure 8:
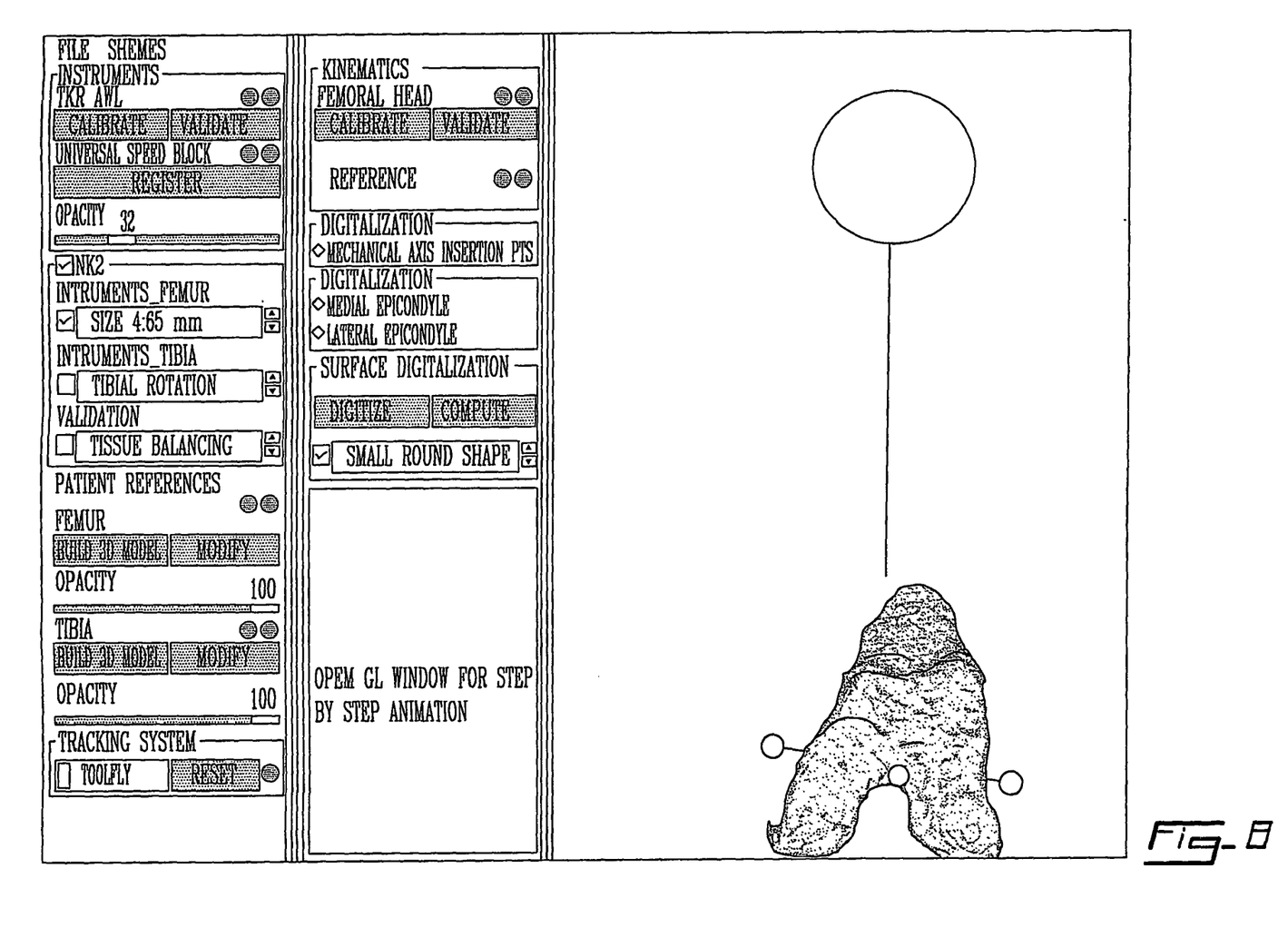
FIG. 8 shows the reconstructed bone after morphing.

From the input data gathered, the approximate model reconstruction can be morphed into an actual three-dimensional model. FIG. 8 demonstrates what a smoothed over surface can look like. Once this reconstruction is done, tools used for the surgery can be tracked with respect to this model, thereby allowing the surgeon to navigate with tools and have a reference in the body.

Figure 9:
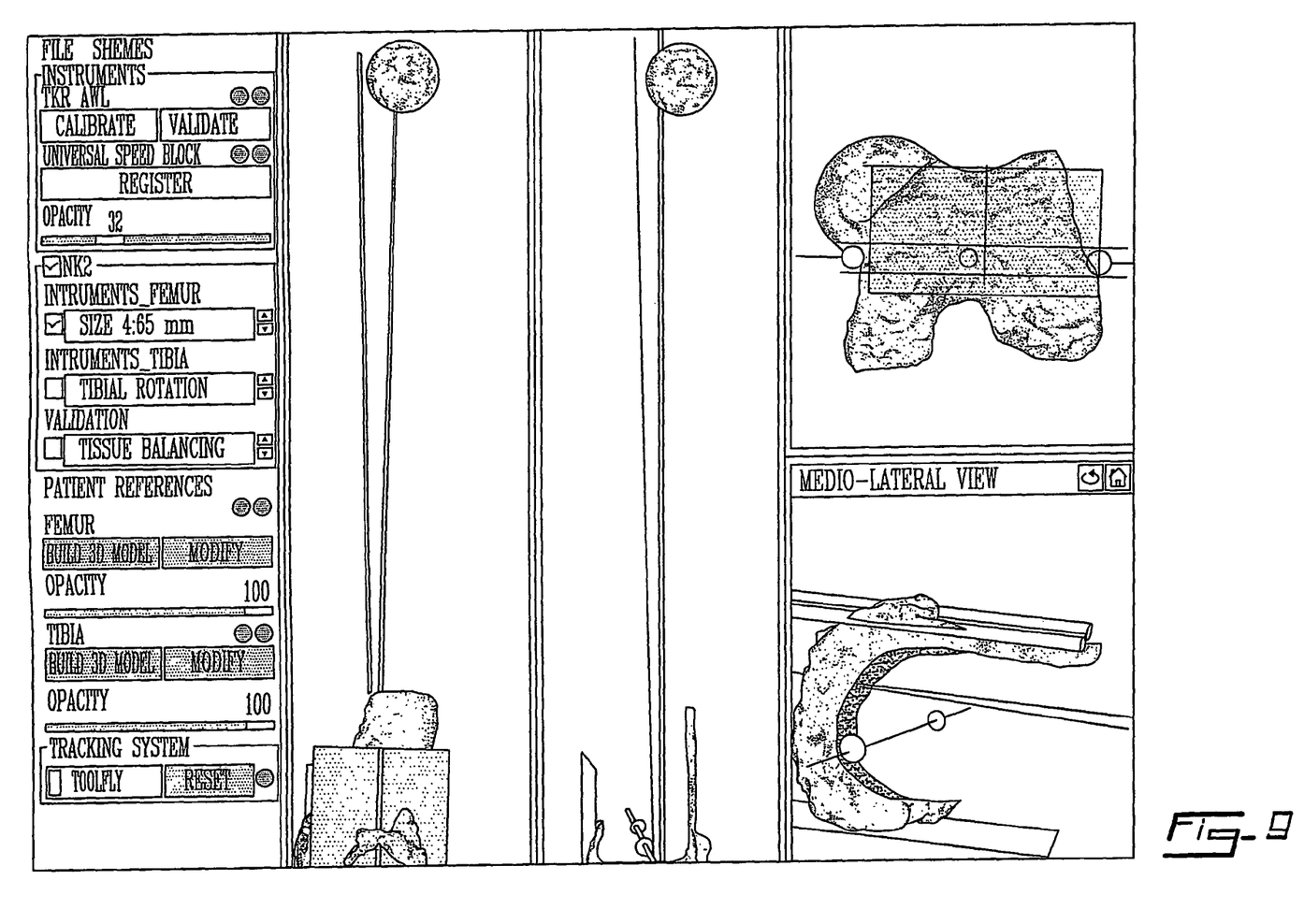
FIG. 9 shows the placing of the cutting guide.

Once two axes have been calculated and a reference system has been established for the femur and the tibia, it is now possible to determine the cutting planes for the cut the surgeon must make of the femur bone. The cutting planes are determined in order to properly install the cutting guide on the patient. FIG. 9 shows how a model of the cutting guide is displayed on the output device, along with the calculated axes and the reconstructed bone model. Using this model, the surgeon selects the position of the cutting guide. A feature displays the angle between the mechanical axis and the cutting guide allows the surgeon to reach a good level of accuracy. Some of the navigation options include sizing, cut validation, axial rotation, and preview of cuts, posterior slope, and rotation alignment. Soft tissue and gap balancing is also an option to restore the global alignment of the limb while assuring a good stability in flexion and in extension.

Figure 10:
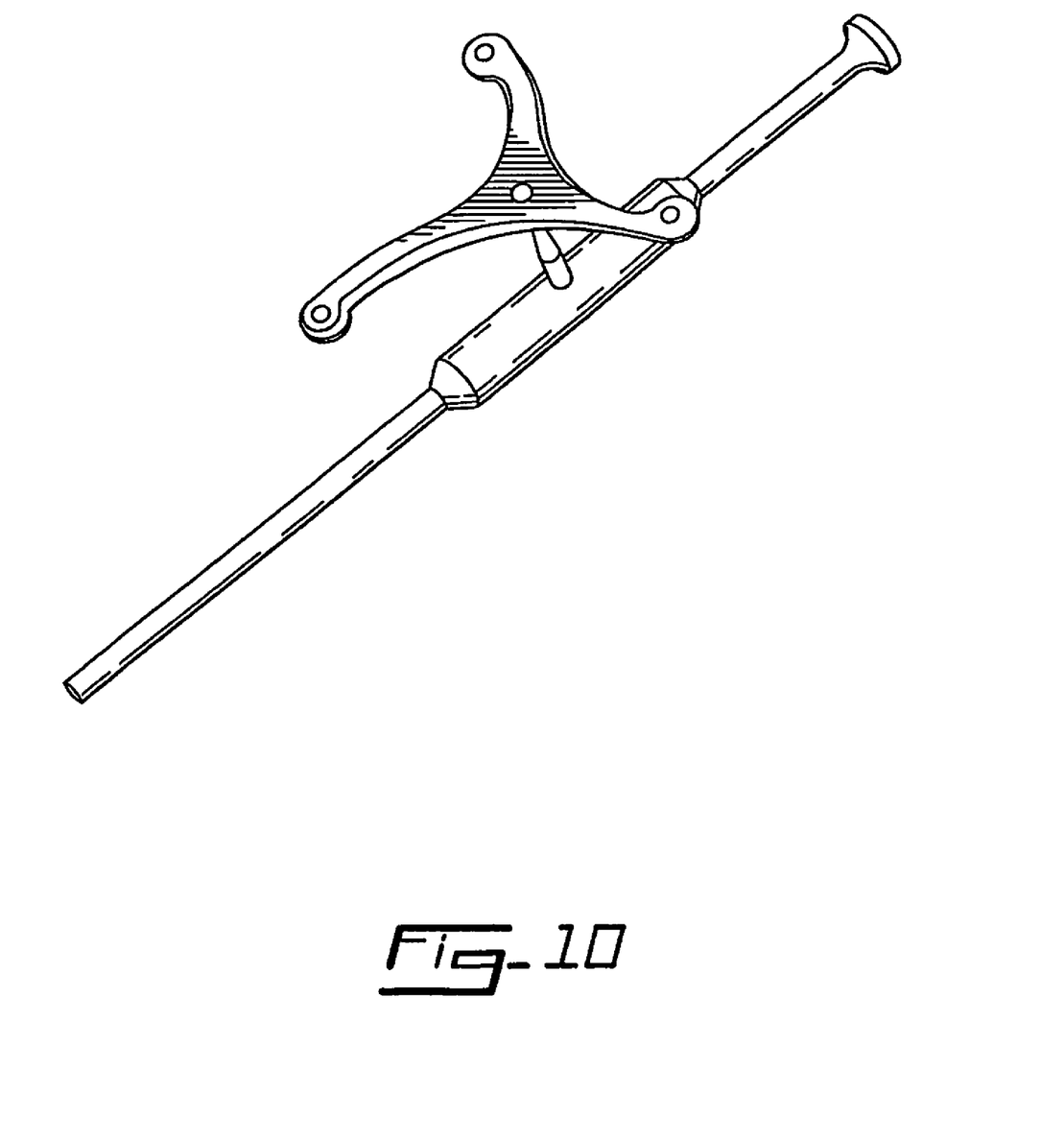
FIG. 10 is a diagram of a registration tool with an adaptive tip.

FIG. 10 is the preferred embodiment of the registration tool to be used in the digitizing process. The tool is equipped with a position-sensing device, such as those known in the field of tracking, having three position identifying devices. In this embodiment, both ends of the tool can serve as a digitizing tip, each end having a different radius. The smaller end can be used on anatomical surfaces that do not easily accommodate the flat surface of the tool. The larger end can be used on flatter anatomical surfaces. The user selects on the computer which end is used. Alternatively, there can be automatic detection of the end being used, such as the computer recognizing the radius of the disc surface when it is placed on the bone surface. For the actual registration of the small surfaces, this can be achieved in several ways. For example, there can be a button on the tool that controls the digitizing. Alternatively, this can be done by pressing a key on a keyboard to select a point to be digitized. Also alternatively, digitizing can be triggered by a rotating action of the tool by a quarter turn. It can be appreciated that alternative embodiments for the registration tool are possible. For example, other multi-purpose combinations can be made. One end can be an awl, a screwdriver, or a probe, while the other end is a digitizer. Similarly, the tool can be a single-ended digitizer as well.

FIG. 11 illustrates a leg with the soft tissues of the knees balanced. The femur 1 and tibia 2 are perfectly aligned such that the mechanical axis ⊕ is aligned as it should anatomically be. The mechanical axis begins at the center of the femoral head 3, goes through the center of the inter-condylar notch 4 of the femur, continues through the center of the top of the tibia 5, and ends at the center of the ankle 6. For this to occur, the medial and lateral tissues must be correctly tensioned when the knee is in full extension.

Figure 12:
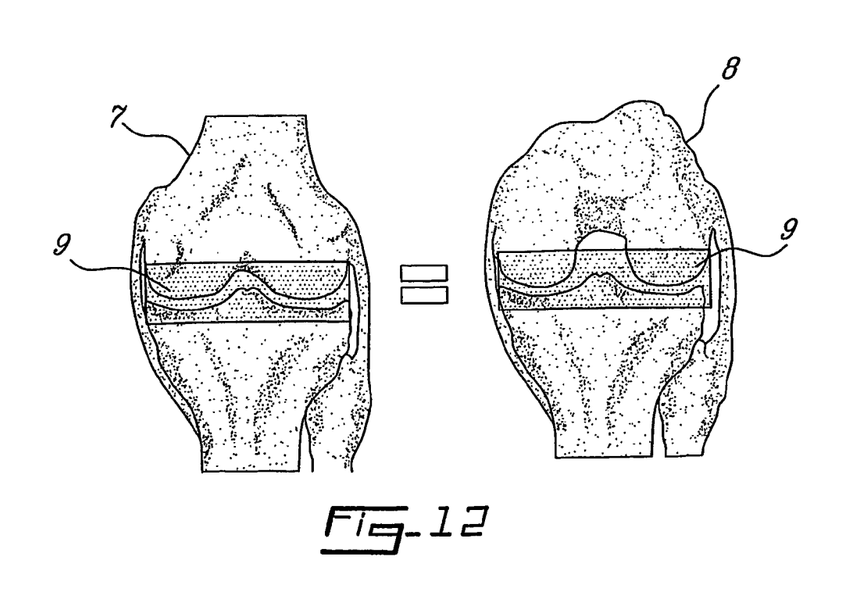
FIG. 12 is an illustration showing a symmetric gap in flexion and extension.

FIG. 12 is an illustration that shows that a knee in extension 7 has the same gap as a knee in flexion 8. The gap will result after the tibial and femoral cuts have been performed and can be seen as the shaded rectangular area 9 shown in the figure. As can be seen from the figure, the portion of the gap 9 from the tibia is equivalent in both positions of the knee (extension and flexion) whereas the portion of the gap 9 from the femur is different when the knee is in one position versus the other.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for determining a distal cut thickness and posterior cut thickness for a femur in a knee replacement operation, the method comprising:
    performing a tibial cut on a tibia;
    performing soft tissue balancing based on a desired limb alignment;
    creating a reference coordinate system in a computer aided surgery system for an uncut femur and said tibia;
    registering said femur and said tibia to said reference coordinate system using tracking devices;
    measuring an extension gap between said femur and said tibial cut while in extension using said femur and tibia as registered in said reference coordinate system;
    measuring a flexion gap between said femur and said tibial cut while in flexion using said femur and tibia as registered in said reference coordinate system;
    calculating a distal cut thickness and a posterior cut thickness for said femur using said measured extension gap and said measured flexion gap and taking into account a distal thickness and posterior thickness of a femoral implant; and
    performing said femoral posterior cut according to said posterior cut thickness subsequently to the calculating of the posterior cut thickness; and
    performing said femoral distal cut according to said distal cut thickness and based on the flexion gap resulting from the performed femoral posterior cut registered in said reference coordinate system.

2. A method as claimed in claim 1, wherein, said distal cut thickness and said posterior cut thickness are calculated such that a post-cut gap from said tibia to said femur is equal in extension and in flexion.

3. A method as claimed in claim 2, wherein said performing a tibial cut comprises obtaining a tibial cut that is substantially perpendicular to a mechanical axis of said limb.

4. A method as claimed in claim 3, wherein said performing a tibial cut comprises using a positioning device to align said substantially perpendicular cut.

5. A method as claimed in claim 1, wherein said performing a femoral cut comprises obtaining a femoral cut that is substantially parallel to said tibial cut such that said extension gap and said flexion gap are substantially rectangular after said femoral cut has been done.

6. A method as claimed in claim 1, wherein said taking into account a distal thickness and posterior thickness comprises selecting a femoral implant having a distal thickness and a posterior thickness such that a desired distal cut thickness and posterior cut thickness may be obtained.

7. A method as claimed in claim 1, wherein said performing a tibial cut comprises registering said tibial cut to said reference coordinate system.

8. A method as claimed in claim 7, wherein said performing soft tissue balancing comprises spacing said femur and said tibia while in extension.

9. A method as claimed in claim 8, wherein said spacing comprises placing a tensor device between said femur and said tibia and tensing ligaments connecting said femur and said tibia.

10. A method as claimed in claim 7, wherein said desired limb alignment is based on a computed limb alignment.

11. A method as claimed in claim 7, wherein said measuring a flexion gap and measuring an extension gap comprises using said tracking devices to obtain said measurements.

12. A method as claimed in claim 11, wherein said measuring a flexion gap comprises determining a most posterior point of a reference of said femur on said reference coordinate system and measuring a distance between said tibial cut and said most posterior point of said femur.

13. A method as claimed in claim 12, wherein said registering said cut comprises creating a plane along said tibial cut on said reference coordinate system and said determining a most posterior point of a reference comprises raising said plane on said tibial cut until said most posterior point of said femur is reached.

* * * * *